United States Patent
Detty et al.

(10) Patent No.: US 6,458,967 B1
(45) Date of Patent: Oct. 1, 2002

(54) METHOD FOR PREPARATION OF AN INTERMEDIATE DYE PRODUCT

(75) Inventors: Michael Ray Detty, Rochester; Peter Robert Virkler, Buffalo, both of NY (US)

(73) Assignee: The Research Foundation of State University of New York, Buffalo, NY (US)

( * ) Notice: Subject to any disclaimer, the term of this patent is extended or adjusted under 35 U.S.C. 154(b) by 0 days.

(21) Appl. No.: 09/886,974

(22) Filed: Jun. 22, 2001

Related U.S. Application Data

(60) Provisional application No. 60/214,190, filed on Jun. 26, 2000.

(51) Int. Cl.$^7$ .............................................. C07D 335/00
(52) U.S. Cl. ........................................................ 549/13
(58) Field of Search ............................................ 549/13

(56) References Cited

U.S. PATENT DOCUMENTS

| | | | |
|---|---|---|---|
| 4,283,475 A | 8/1981 | Kawamura et al. | 430/70 |
| 5,403,626 A | 4/1995 | Bugner et al. | 430/58 |
| 5,919,950 A | 7/1999 | Garcia et al. | 549/13 |
| 6,008,350 A | * 12/1999 | Roschger et al. | 544/300 |
| 6,022,961 A | * 2/2000 | Yamamoto et al. | 536/24.3 |
| 6,110,646 A | 8/2000 | Urano et al. | 430/302 |

* cited by examiner

*Primary Examiner*—Deborah C. Lambkin
(74) *Attorney, Agent, or Firm*—Hudgson Russ LLP

(57) ABSTRACT

The present invention provides a novel method for the synthesis of an intermediate dye product having the following formula:

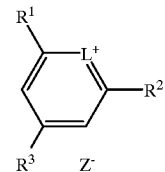

wherein
  L is S, Te, or Se;
  $R^1$ and $R^2$ are either the same or different aryl or alkyl compounds;
  $R^3$ is hydrogen or a short chain alkyl group; and
  Z is an anion.

The process to formulate this intermediate compound entails reacting an $R^1$-acetylene compound with an $R^2$-acetylene compound (compounds A) into an enol ether compound with the $R^1$ and/or $R^2$ constituents (compound D). And from compound D, it forms into an intermediate dye compound having an L-based cyclic ring with the $R^1$ and/or $R^2$ constituents (compound F). With compound F the desired dye can be made with a greater overall yield for mass production.

15 Claims, No Drawings

METHOD FOR PREPARATION OF AN INTERMEDIATE DYE PRODUCT

CLAIM OF PRIORITY

This application claims priority to U.S. Provisional Patent application Ser. No. 60/214,190, filed on Jun. 26, 2000.

FIELD OF THE INVENTION

The present invention relates generally to the field of dyes useful in image recording.

DESCRIPTION OF RELATED ART

Kawamura et al. in U.S. Pat. No. 4,283,475 discloses a 2,6-di-t-butyl-4-[5-(2,6-di-t-butyl-4H-thiopyran-4-ylidene) penta-1,3-dienyl]thiopyrylium salts, and a process for production thereof. In particular, Kawamura et al. disclose 2,6-di-tert-butylthiopyrylium pentamethine hexafluorophosphate dye, as shown immediately below and identified as Compound (I), and variations of that dye. The variations alter the letter A from hydrogen to various other compounds disclosed in the '475 patent.

Compound (I)

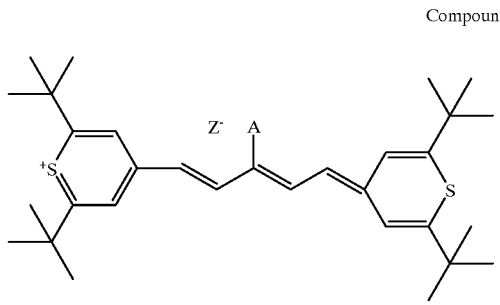

The thiopyrylium pentamethine dye of compound (I) has properties that make it a useful laser dye. For example, it has an absorption maximum of 822 nm in dichloromethane. This wavelength is compatible with gallium-arsenide diode lasers and other light sources emitting near 830 nm. Compound (I) also has an extinction coefficient in dichloromethane of 384,000 $M^{-1}cm^{-1}$ at the absorption maximum and displays little crystallization in coated formats. These properties make compound (I) and variations thereof an ideal material for use as the heat-generating element in coated formats for thermal imaging, lithography, optical recording, and related imaging applications. Accordingly, compound (I) and its variations thereof are desired. The process to make these salts is set forth by Kawamura et al. In particular, Kawamura et al. disclose that the process is as follows: "Compound (i) [as shown immediately below] is heated in the presence of phosphorus pentasulfide at Step (1) . . . to obtain compound (ii). The reaction product, Compound (ii) is then reacted with alkali hydrosulfide such as potassium hydrosulfide in a solvent at a temperature between 50° C. to 200° C. in an atmosphere of an inert and oxygen-free gas such as $N_2$, $CO_2$, and argon gas (Step 2) to produce compound (iii). The solvent used at Step 2 is water-free and non aqueous solvent having at least 20 of dielectric constant and at least 2 of dipole moment, for example, hexamethyl phosphoric triamide, dimethylsulfoxide, N,N-dimethylformamide or N-methylpyrrolidone. The alkali sulfide or alkali hydrosulfide used is 1 to 30 moles, preferably 3 to 20 moles, per 1 mole of compound (ii). Compound (iii) is then reacted with an alkylating agent at Step 3 to obtain compound (iv) which is then hydrolyzed to form compound (v) [Step 4]. The reaction temperature at Step (3) is −10° C. to 200° C., preferably 40° C. to 100° C. and the reaction time is 30 minutes to 2 hours. In formula (iv), $R_4$ is an alkyl or substituted alkyl group derived from the alkylating agent. Compound (v) is subjected to the action of a Grignard reagent at a temperature of −20° C. to 25° C. for 30 to 90 minutes in a solvent and in a nonoxidizing atmosphere and then treated with an acid to form compound (II) (Step 5)."

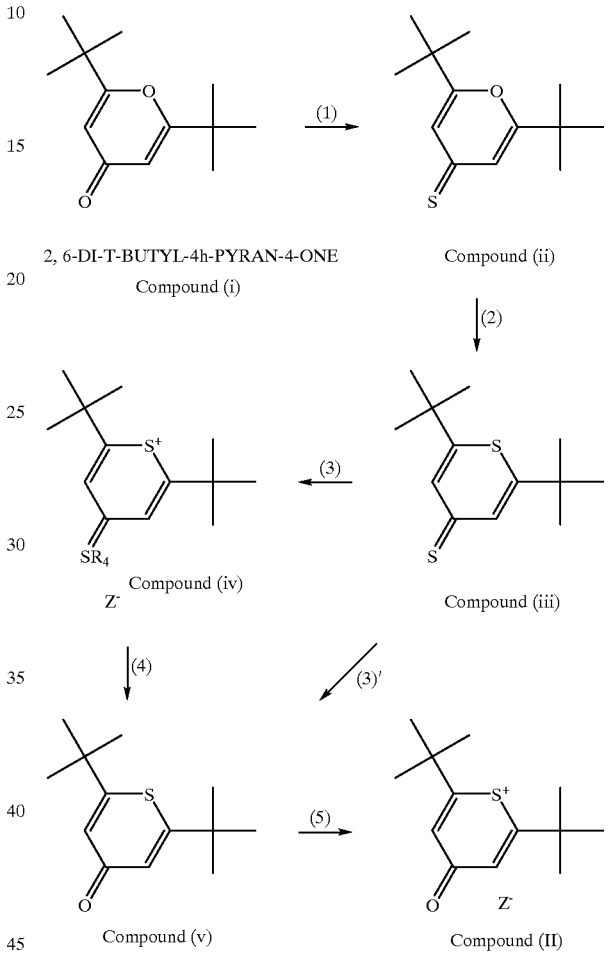

Compound (II) is known as 2,6,-di-t-butyl-4-methylthiopyrylium salt. To obtain the desired 2,6-di-t-butyl-4-[5-(2,6-di-t-butyl-4H-thiopyran-4-ylidene)penta-1,3-dienyl]thiopyrylium salts and in particular 2,6-di-tert-butylthiopyrylium pentamethine hexafluorophosphate, compound (II) is reacted with a 1-phenylamino-3-phenylimino-1-propene, as shown immediately below and identified as compound (III), or a salt of the compound (III) with an acid.

Compound (III)

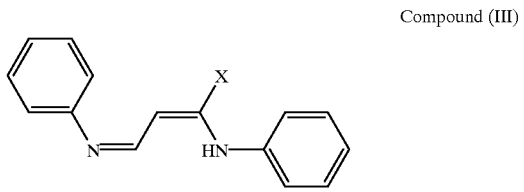

The '457 patent disclosed that the "preferred examples of the compound of formula (III) are 1-phenylamino-3- phenylimino-1-propene, 2-benzyl-1-phenylamino-3-phenylimino-1-propene, 2-phenyl-1-phenylamino-3-phenylimino-1-propene, 2-bromo- or 2-chloro-1-phenylamino-3-phenylimino-1-propene, and 2-ethyl-1-phenylamino-3-phenylimino-1-propene.

The acid forming a salt with the compound (III) is an acid having a pKa generally not more than 4, preferably not more than 1, and includes, for example, hydrochloric acid, hydrobromic acid and sulfuric acid.

The reaction of compounds (II) and (III) is carried out either in a carboxylic acid anhydride or in an amine. When the reaction is carried out in the carboxylic acid anhydride, the carboxylic acid anhydride contributes to the reaction system as an aniline-eliminating agent. As a carboxylic acid anhydride an aliphatic carboxylic acid anhydride containing 4 to 16 carbon atoms and which may be substituted with one or more substituents, may be used. The substituents include halogen atoms, such as fluorine and chlorine. Specific examples of the carboxylic acid anhydride include acetic acid anhydride, propionic acid anhydride and trifluoro acetic acid anhydride. In order to dissolve the reaction materials, there may be added an auxiliary solvent which does not react with the raw materials, the carboxylic acid anhydride, the base described hereinafter and the reaction product in the reaction system, such as acetic acid or nitrobenzene. This reaction requires the presence of a base. The base is generally an organic base, for example alkali metal acetates such as sodium acetate or potassium acetate; alkylamines, preferably primary amines having 1 to 10 carbon atoms, secondary amines having 2 to 20 carbon atoms total or tertiary amines having 3 to 30 carbon atoms; aromatic amines; and nitrogen-containing aromatic amines. Specific examples are triethylamine, piperidine, aniline, dimethylaniline, pyridine, and quinoline.

The amount of the base used is 0.2 to 100 moles, preferably 0.5 to 20 moles, per mole of the 2,6-di-t-butyl-4-methylthiopyrylium salt. The weight ratio of the carboxylic acid anhydride to the 2,6-di-t-butyl-4-methylthiopyrylium salt is 0.1–100:1, preferably 1–50:1.

When the reaction is carried out in an amine, an auxiliary solvent such as acetic acid or nitro-benzene may likewise be added. The amine used in this reaction may be the same as those exemplified above as the base. The amount of amine is generally about 0.5 to 200 moles, preferably 1 to 100 moles per mole of the 2,6-di-t-butyl-4-methylthiopyrylium salt.

This process is generally carried out at about 50° to 200° C., preferably 80° to 140° C. The amounts of compounds (II) and (III) may be stoichiometric. Generally, about 0.3 to 1 mole of the 1-phenylamino-3-phenylimino-1-propene is used per mole of the 2,6-di-t-butyl-4-methylthiopyrylium salt. The reaction time varies depending upon the reaction temperature, the type of the solvent, etc., but is generally 1 minute to 1 hour."

This process, however, is not economically viable because the overall yield of the critical compound (II) for the formation of compound (I) is below 30%, see synthesis example for compound (II) at columns 11 and 12 of the '475 patent. Accordingly, there is a need to make compound (II) at significantly higher overall yields to make compound (I) and variations thereof economically viable. This invention solves this problem.

SUMMARY OF THE INVENTION

The present invention provides a novel method for the synthesis of an intermediate dye product having the following formula:

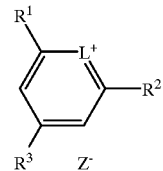

wherein

L is S, Te, or Se;

$R^1$ and $R^2$ are either the same or different aryl or alkyl compounds;

$R^3$ is hydrogen or a short chain alkyl group; and

Z is an anion.

The process to formulate this intermediate compound entails reacting an $R^1$-acetylene compound with an $R^2$-acetylene compound (compounds A) into an enol ether compound with the $R^1$ and/or $R^2$ constituents (compound D). And from compound D, it forms into an intermediate dye compound having an L-based cyclic ring with the $R^1$ and/or $R^2$ constituents (compound F). With compound F the desired dye can be made with a greater overall yield for mass production.

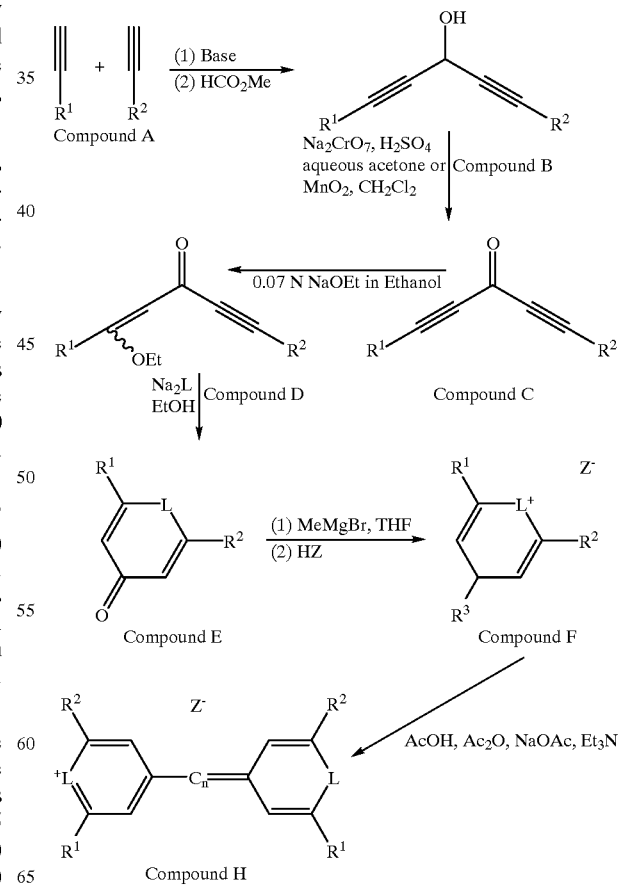

DETAILED DESCRIPTION OF THE INVENTION

The present invention describes the synthesis of an intermediate dye compound (identified above as compound F) from an acetylene product (identified above as compound A). Compound F has the following formula:

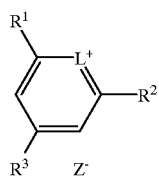

wherein

L is S, Te, or Se;

$R^1$ and $R^2$ are either the same or different aryl or alkyl compounds;

$R^3$ is hydrogen or a short chain alkyl group; and

Z is an anion.

In particular, $R^1$ and $R^2$ are aryl, and/or linear or branched alkyl groups having 1 to 15 carbon atoms, preferably 1 to 5 carbon atoms. Examples of such groups include, and are not limited to, methyl, ethyl, isopropyl, t-butyl, pentyl groups, phenyl, tolyl, ethylphenyl, naphthyl and variations thereof. The variations may be substituted with other aryl groups having (a) 6 to 15 carbon atoms, preferably 9 to 13 carbon atoms such as phenyl, tolyl, ethylphenyl and naphthyl groups; (b) halogen atoms, that is chlorine, bromine, fluorine and iodine; and (c) alkoxy groups having 1 to 5 carbon atoms, preferably 1 to 3 carbon atoms, such as a methoxy group.

Also the anion identified as Z can be a single atomic ion or atomic grouping ions composed of a plurality of atoms which have a negative charge. Anions of strong acids represented by HZ and having a pKa of not more than 5, especially not more than 2, are preferred for easy synthesis of the thiopyrylium salts. Specific examples of the anions are single atomic ions such as halogen anions, e.g. fluoride, chloride, bromide and iodide ions; and ionic groups, for example organic anions such as trifluoroacetate, trichloroacetate and p-toluenesulfonate ions, and inorganic anions such as perchlorate, periodate, tetrachloroaluminate, trichloroferrate (II), tetrafluoroborate, hexafluorophosphate, sulfate, hydrogensulfate and nitrate ions. Divalent anions are interpreted, as a matter of formality, such that 1/2 of such an anion represents a monovalent anion.

The process of synthesis of compound F is as follows:

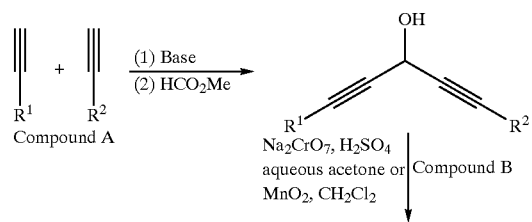

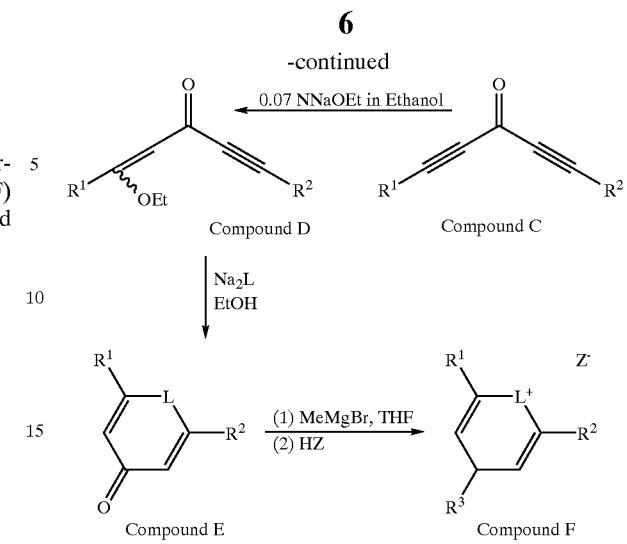

In principle, compound E, which would be thiopyranone if L were Sulfur, should be readily prepared from diynone, compound C, by the addition of hydrogen sulfide. However, as shown below, the addition of hydrogen sulfide gas to ethanol solutions of compound C generate mixtures of thiopyranone, compound E, and dihydrothiophene, compound G, with compound G being the major product. The separation of compounds E and G requires a chromatographic separation.

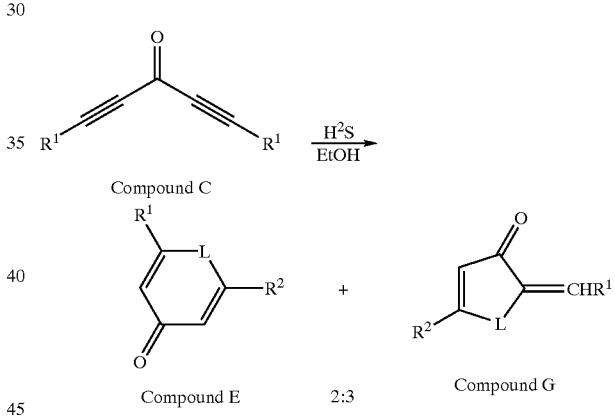

The formation of compound G can be avoided completely by converting the compound C to a mixture of enol ethers (compound D) by the careful addition of ethanol across one of the triple bonds of compound C to a mixture of enol ethers. That careful addition of ethanol across one of the triple bonds of compound C is an 0.07 M sodium ethoxide in ethanol. Addition of sodium sulfide or sodium hydrosulfide to the enol ethers, compound D, (both stereoisomers are observed in an 84:16 ratio) gives thiopyranone (compound E), if L is Sulfur, as the only heterocyclic product, which is isolated as a crystalline product from the crude reaction mixture.

Alternatively, the addition of sodium selenopyrylium or sodium telluropyrylium generates a compound D wherein the element L is respectively selenopyrylium or telluropyrylium.

Compound E then converts to compound F. This conversion occurs after compound F is (1) dissolved in tetrahydrofuran (THF), (2) mixed with methylmagnesium bromide in ether, and (3) then the desired anionic solution HZ is added.

Once compound F is formed, the desired dye can be fabricated, in this case compound H is illustrated below as 2,6-$R^1,R^2$ thiopyrylium pentamethine with an anion, Z:

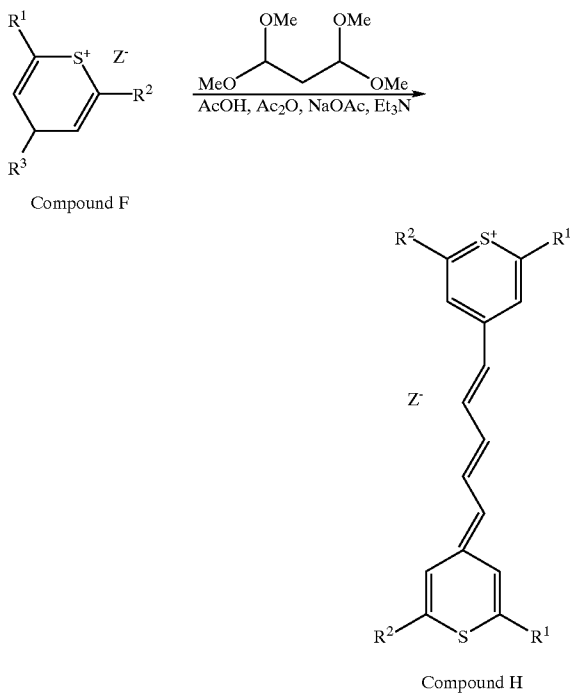

Compound F

Compound H

The process to generate compound H as 2,6-$R^1,R^2$ thiopyrylium pentamethine with an anion, uses triethylamine and 1,1,3,3-tetramethoxypropane to form the pentamethine unit. Obviously, the methine chain between the pyrylium groups can have various chain lengths. In particular, the range of the methine chain can be from 1 to 5 carbons depending on which product is used to form the compound H.

The standard recipe for use of 1,1,3,3-tetramethoxypropane with active methyl compounds such as 4-methylthiopyrylium salt (compound F if L is Sulfur) is to use an alcohol as solvent (typically ethanol) with acid catalysis (5% hydrochloric acid). Use of hydrochloric acid catalysis in ethanol gave <5% isolated yield of compound H. Alternatively, similar reactions with bis anilinium salts of 1,3-propanedial as electrophile use sodium acetate in a mixed solvent of acetic acid and acetic anhydride to affect deprotonation of the 4-methylthiopyrylium salt and addition to the electrophile to form a polymethine dye. We found unexpectedly that addition of triethylamine to the 4-methylthiopyrylium salt (compound F) in the sodium acetate/acetic acid/acetic anhydride mixture gives appropriate buffering to eliminate methanol from the 1,1,3,3-tetramethoxypropane to generate the electrophile in situ. Isolated yields of compound F were 94%. Using sodium acetate as the only base gave <5% yield of dye as did the use of pyridine as base.

This procedure is applicable to the synthesis of other thiopyrylium mono, di, tri, buta, or pentamethine dyes starting with appropriate acetylenic starting materials. Selenopyrylium and telluropyrylium analogs of these dyes can be prepared as well.

EXAMPLES

I. The following example of preparation of 2,6-di-tert-butylthiopyrylium pentamethine hexafluorophosphate dye, is presented for illustrative purposes and not meant to be restrictive.

Preparation of 1,5-Di-tert-butyl-1,4-pentadiyn-3-ol (Compound B)

Tert-Butylacetylene (41.0 grams, 0.500 mole) was dissolved in 1 L of dry tetrahydrofuran in a 5-L flask under an inert atmosphere of argon or nitrogen. The resulting solution was cooled to 0° C. in an ice water bath. To the cold solution was slowly added 1.0 mole of a strong base to deprotonate the tert-butyl acetylene with stirring with the addition slow enough to maintain the temperature of the reaction mixture at or below 10EC. Typically, either 200 mL of 2.5 M n-butyllithium in hexane (0.50 mole) or 167 mL of 3.0 M methylmagnesium bromide (0.50 mole) in ether gave identical results. After the slow addition of the base, the reaction mixture was stirred 1 hour at 0° C. Methyl formate (16.5 grams, 0.275 mole) was added slowly and the resulting mixture was allowed to warm to ambient temperature with stirring. The reaction was quenched by the addition of 2 L of water. The products were extracted with ether (4×500 mL). The combined ether extracts were washed with brine (2×1 L), dried over magnesium sulfate, filtered, and concentrated. The crystalline residue was recrystallized from hexanes to give 43.2 grams (90% of theoretical) of 1,5-di-tert-butyl-1,4-pentadiyn-3-ol: Melting point 67–70° C.; $^1$H NMR (deuteriochloroform) d 5.09 (d, 1 H, J=6.5 Hz), 2.03 (d, 1 H, J=6.5 Hz), 1.285 (s, 18H).

Those skilled in the art will recognize that other strong bases, such as lithium diisopropylamide, lithium hexamethyldisilazide, ethylmagnesium bromide, methyllithium, or sec-butyllithium should work equally well.

Preparation of 1,5-Di-tert-butyl-1,4-pentadiyn-3-one (Compound C)

A solution of 48.0 grams (0.25 mole of compound B in 500 mL of acetone contained in a 2-L Erlenmeyer flask was cooled to 0° C. in an ice-water bath. To this solution, 500 mL of a 10% chromic acid solution (prepared by the addition of 75 grams of sulfuric acid to 50 grams of sodium dichromate in 550 grams of ice was added slowly. After addition was complete, the reaction mixture was warmed to ambient temperature where stirring was continued for 0.5 h. The reaction mixture was poured into water (1 L) and the products were extracted with ether (3×500 mL). The combined ether extracts were washed with brine (2×500 mL), dried over magnesium sulfate, filtered, and concentrated. The crystalline residue was recrystallized from hexanes to give 47.8 grams (92% of theoretical) of 1,5-di-tert-butyl-1, 4-pentadiyn-3-one: Melting point 62–63.5° C.; $^1$H NMR (deuteriochloroform) d 1.285 (s, 18H).

Preparation of 2,6-Di-tert-butylthiopyran-4-one (Compound E)

Diynone, compound C (19.0 grams, 0.100 mole) was dissolved in 500 mL of 0.07 M sodium ethoxide in ethanol. After 3 h of stirring at ambient temperature, the diynone, compound C, was no longer detected by thin layer chromatography. Diynone, compound C, was converted under the reaction conditions to a mixture of enol ethers, compound D. The mixture of enol ethers was added to a solution of disodium sulfide at ambient temperature. The disodium sulfide solution was prepared by the addition of sodium borohydride (2.0 grams, 0.053 mole) in 0.5-gram portions every 0.5 h to a slurry of elemental sulfur (3.5 g, 0.11 mole) in 500 mL of 0.07 M sodium ethoxide in ethanol heated to reflux under an inert atmosphere of nitrogen or argon. After the final addition of the sodium borohydride, the reaction mixture was cooled to ambient temperature before addition of the enol ethers, compound D. After addition of enol ethers D, the reaction mixture was stirred 1 h at ambient temperature and was then poured into 2 L of water. The products were extracted with dichloromethane (3×500 mL) and the combined organic extracts were washed with brine (2×500 mL), dried over magnesium sulfate, filtered, and concentrated. The crude crystalline product was recrystallized from acetonitrile to give 20.2 grams (90% of theoretical) of thiopyranone, compound E: Melting point 96–98° C.; $^1$H NMR (deuteriochloroform): d 6.88 (s, 2H), 1.33 (s, 18 H). Anal. Calculated for $C_{13}H_{20}OS$: C, 69.59; H, 8.49; S, 14.29. Found: C, 69.71; H, 8.49; S, 14.11.

The enol ethers, compound D, were present as an 84:16 mixture. The mixture could be isolated by pouring the reaction mixture into water and extracting with ether. The ether extracts were dried over magnesium sulfate, filtered, and concentrated. The stereochemistry could not be unambiguously assigned.

The major enol ether of the mixture, compound D, gave the following spectral data: $^1$H NMR (deuteriochloroform): δ 5.56 (s, 1H), 4.09 (q, 2 H, J=7 Hz), 1.2 (t, 3 H, J=7 Hz), 1.26 (s, 9 H), 1.12 (s, 9 H); ir (film on sodium chloride): 2201, 1641 $cm^{-1}$.

The minor enol ether of the mixture, compound D, gave the following spectral data: $^1$H NMR (deutheriochloroform): δ 5.38 (s, 1H), 3.82 (q, 2 H, J=7 Hz), 1.34 (t, 3 H, J=7 Hz), 1.25 (s, 9 H), 1.24 (s, 9 H); ir (film on sodium chloride): 2215, 1641 $cm^{-1}$.

The mixture of enol ethers, compound D, gave the following mass spectrum and elemental analysis: ms (ES): m/z 237 ($MH^+$, base peak). Anal. Calculated for $C_{15}H_{24}O_2$: C, 76.19; H, 10.23. Found: C, 76.52; H, 10.44.

Those skilled in the art will recognize that disodium sulfide nonahydrate or sodium hydrosulfide hydrate can be substituted for the disodium sulfide generated in situ. However, yields are significantly lower (67–75%) when these reagents are employed.

Preparation of 2,6-Di-tert-butyl-4-methylthiopyrylium Hexafluorophosphate
(Compound F)

Thiopyranone D (22.4 grams, 0.100 mole) was dissolved in 250 mL of dry tetrahydrofuran. To this solution was added 40 mL of a 3.0 M solution of methylmagnesium bromide (0.12 mole) in ether. After addition was complete, the reaction mixture was heated at reflux for 1 h and was cooled to ambient temperature. The reaction mixture was slowly added with stirring to 1 L of a cold solution of 10% hexafluorophosphoric acid. The solid was collected by filtration and the filter cake was washed with water (2×250 mL) and ether (3×250 mL). The crude white solid was recrystallized from acetonitrile-ether to give 34.1 g (93% of theoretical) of 2,6-di-tert-butyl4-methylthiopyrylium hexafluorophosphate: Melting point 162–166° C.; $^1$H NMR (deuteriochloroform) d 8.45 (s, 2 H), 3.04 (s, 3 H), 1.74 (s, 18 H). Anal. Calculated for $C_{14}H_{23}S-PF_6$: C, 45.65; H, 6.28; S, 8.70. Found: C, 45.50; H, 6.35; S, 8.65.

Preparation of 2,6-Di-tert-butylthiopyrylium Pentamethine Hexafluorophosphate Dye
(Compound H)

Triethylamine (1.76 grams, 2.2 mL, 0.016 mole) was added dropwise to a slurry of 4-methylthiopyrylium salt, compound F, (6.00 grams, 0.0163 mole) and sodium acetate (1.34 grams 0.0160 mole) in 60 mL of acetic acid and 30 mL of acetic anhydride. The resulting mixture was heated with stirring on a steam bath (85° C. for temperature of reaction mixture) and 1,1,3,3-tetramethoxypropane (10.0 grams, 0.064 mole) was added in two 5-gram, portions 45 minutes apart. After the second addition, the reaction mixture was heated on the steam bath with stirring for 3 h. The reaction mixture was cooled to ambient temperature and poured into 300 mL of a 5% hexafluorophosphoric acid solution. The metallic purple solid was collected by filtration and the filter cake was washed with 300 mL of water. The crude dye was dissolved in a minimal amount of acetonitrile (≈10–15 mL) and the resulting solution was diluted with approximately 150 mL of ether. The metallic bronze crystals were collected by filtration and dried to give 9.59 grams (94% of theoretical) of dye 1: $^1$H NMR (deuteriochloroform) d 8.13 (t, 2 H, J=13 Hz), 7.43 (br s, 4 H), 6.48 (t, 1 H, J=13 Hz) 6.25 (d, 2 H, J=13 Hz), 1.42 (s, 18 H); $l_{max}$ 822 nm [Î=(384,000±7,500) $M^{-1}$ $cm^{-1}$). Anal. Calculated for $C_{31}H_{45}S_2-PF_6$: C, 59.41; H, 7.24; S, 10.23. Found: C, 59.33; H, 7.28; S, 9.93.

Compound H is chloroform soluble while 4-methylthiopyrylium salt, compound F, is not. If unreacted 4methylthiopyrylium salt, compound F, is present at the end of reaction, the filter cake can be washed with chloroform. Compound H will be found in the filtrate while unreacted thiopyrylium salt, compound F, will be left on the filter. Successful reactions will have an emerald green color as the reaction progresses while unsuccessful reactions will turn blue.

II. Synthesis of Analogs. For the synthesis of selenopyrylium analog, the mixture of enol ethers, compound D, is treated with disodium selenide instead of disodium sulfide. The disodium selenide solution was prepared by the addition of sodium borohydride (2.0 grams, 0.053 mole) in 0.5-gram portions every 0.5 h to a slurry of elemental selenium (8.7 g, 0.11 mole) in 500 mL of 0.07 M sodium ethoxide in ethanol heated to reflux under an inert atmosphere of nitrogen or argon. After the final addition of the sodium borohydride, the reaction mixture was cooled to ambient temperature before addition of the enol ethers, compound D. After addition of enol ethers, compound D, the reaction mixture was stirred 1 h at ambient temperature and was then poured into 2 L of water. The products were extracted with dichloromethane (3×500 mL) and the combined organic extracts were washed with brine (2×500 mL), dried over magnesium sulfate, filtered, and concentrated. The crude crystalline product was recrystallized from acetonitrile to give 20.2 grams (90% of theoretical) of 2.6-di-tert-butylselenopyran-4-one, compound E: Melting point 98–102° C.; $^1$H NMR (deuteriochloroform): d 6.96 (s, 2H), 1.36 (s, 18 H). Anal. Calculated for $C_{13}H_{20}OSe$: C, 57.56; H, 7.43. Found: C, 57.71; H, 7.45.

Preparation of 2,6-Di-tert-butyl-4-methylselenopyrylium Hexafluorophosphate
(Compound F)

2,6-Di-tert-butylselenopyran-4-one, compound E, (27.1 grams, 0.100 mole) was dissolved in 250 mL of dry tetrahydrofuran. To this solution was added 40 mL of a 3.0 M solution of methylmagnesium bromide (0.12 mole) in ether. After addition was complete, the reaction mixture was heated at reflux for 1 h and was cooled to ambient temperature. The reaction mixture was slowly added with stirring to 1 L of a cold solution of 10% hexafluorophosphoric acid. The solid was collected by filtration and the filter cake was washed with water (2×250 mL) and ether (3×250 mL). The crude white solid was recrystallized from acetonitrile-ether to give 28.0 g (76% of theoretical) of 2,6-di-tert-butyl-4-methylselenopyrylium hexafluorophosphate, compound F: Melting point 203–204° C.; $^1$H NMR (deuteriochloroform) d 8.34 (s, 2 H), 2.83 (s, 3 H), 1.66 (s, 18 H). Anal. Calculated for $C_{14}H_{23}Se$-$PF_6$: C, 40.50; H, 5.58. Found: C, 40.51; H, 5.35.

Preparation of 2,6-Di-tert-butylselenopyrylium Pentamethine Hexafluorophosphate Dye (Compound H)

1,1,3,3-Tetramethoxypropane (16.0 mL, 0.110 mole) and aniline (22.4 mL, 0.24 mole) were dissolved in 80 mL of acetic acid. The resulting solution was heated to 80° C. for 15 minutes and the reaction mixture was removed from the heating source. A 60% solution of hexafluorophosphoric acid (16 mL, 0.105 mole) was slowly added. After addition was complete, the reaction mixture was poured into 1.5 L of water and the yellow-orange solid was collected by filtration and dried to give the anilinium hexafluorophosphate salt of 1,1,3,3-tetramethoxypropane. 2,6-Di-tert-butyl-4-methylselenopyrylium hexafluorophosphate, compound F, (4.56 g, 0.0110 mol), sodium acetate (1.0 g, 0.012 mole), and the anilinium salt (1.84 g, 0.00500 mol) were heated to 90–95° C. in 50 mL of acetic anhydride for 1 h. The reaction mixture was poured into 300 mL of ether and chilled. The metallic copper-bronze crystals were collected by filtration and dried to give 3.24 g (90%) of Selenium analogue dye, compound H: Melting point 207–210° C.; $l_{max}$ 865 nm [Î=(315,000±6,500) $M^{-1}$ $cm^{-1}$]. Anal. Calculated for $C_{31}H_{45}Se_2$-$PF_6$: C, 51.71; H, 6.30. Found: C, 51.51; H, 6.42.

III. Preparation of 2,6-Di-tert-butylselenopyrylium/ Thiopyrylium Pentamethine Rexafluorophosphate Dye (Dye 1—Compound H)

2,6-Di-tert-butyl-4-methylthiopyrylium hexafluorophosphate, compound F, (0.50 g, 0.00136 mole) and the anilinium hexafluorophosphate salt of 1,1,3,3-tetramethoxypropane (0.60 g, 0.00163 mole) in 10 mL of acetic anhydride were heated at 95° C. for 2.5 h. 2,6-Di-tert-butyl-4-methylselenopyrylium hexafluorophosphate, compound F, (0.56 g, 0.00136 mole) and sodium acetate (0.50 g, 0.0060 mole) were added to the reaction mixture, which was then heated for 15 minutes at 95° C. The reaction mixture was poured into 150 mL of ether and the resulting solution was chilled. Dye 3 was collected by filtration to give 0.41 g (45%) of Dye 3: Melting point 199–201° C.; $l_{max}$ 844 nm [Î=(315,000±6,500) $M^{-1}$ $cm^{-1}$]. Anal. Calculated for $C_{31}H_{45}SSe$-$PF_6$: C, 55.32; H, 6.71. Found: C, 55.33; H, 6.63.

IV. Xylene-phenyl Dye 1-(Trimethylsilylethynyl)-2,6-dimethylphenyl:

($C_{13}H_{18}Si$), FW=202.37 g/mol: 2-Bromo-m-xylene (1.00 g, 5.43 mmol), copper iodide (0.02 g, 0.11 mmol), triphenylphosphine (0.07 g, 0.27 mmol), and bis(triphenylphosphine)palladium(II) chloride (0.08 g, 0.11 mmol) were dissolved in piperidine (7 mL). (Trimethylsilyl)acetylene (compound A) (0.69 g, 7.03 mmol) was added and the reaction mixture was stirred at reflux for 6 hours. Once the reaction was complete, the reaction mixture was filtered through celite and extracted with water and hexanes. The hexanes were washed with brine, dried over magnesium sulfate and concentrated, yielding a yellow liquid which was taken on without purification. $R_f$ 0.75 (hexanes) $^1$H NMR (500 MHz, $CDCl_3$, ppm) d 7.06 (Ar, m, 1H), 7.00 (d, 2H, J=7.00 Hz), 2.41 (s, 6H), 0.25 (s, 9H).

1-(Ethynyl)-2,6-dimethylphenyl:

($C_{10}H_{10}$), FW=130.19 g/mol. 4-(Trimethylsilylethynyl)-isopropylphenyl (10.90 g, 53.8 mmol) was dissolved in tetrahydrofuran (110 mL) and water (11 mL). This reaction mixture was cooled to 0 C and tetrabutylammonium fluoride (17.52 g, 67.0 mmol) was added dropwise. Following this addition, the reaction was stirred at room temperature for 2 hours. The reaction was then extracted with water and hexane. The hexane was dried over magnesium sulfate and concentrated yielding a yellow liquid in 24% yield for the two steps from the 2-bromo-m-xylene. $R_f$ 0.63 (hexanes) $^1$H NMR (500 MHz, $CDCl_3$, ppm) d 7.11 (t, 1H, J=7.5 Hz), 7.02 (d, 2H, J=7.5 Hz), 3.49 (s, 1H), 2.43 (s, 6H); $^{13}$C NMR (125 MHz, $CDCl_3$, ppm) d 140.8, 128.0, 126.6, 121.9, 85.4, 81.1, 20.9.

1-(2,6-Dimethylphenyl)-5-phenyl-1,4-pentadiyn-3-ol:

$C_{19}H_{16}O$, FW=260.33 g/mol. 1-(Ethynyl)-2,6-dimethylphenyl (0.83 g, 6.37 mmol) is dissolved in tetrahydrofuran (12 mL) and cooled to −78° C. A 1.6 M nBuLi (1.10 g, 6.37 mmol) in hexanes was added dropwise and the reaction was warmed to room temperature for 20 minutes. This reaction mixture was then transferred to a solution of phenylpropargyl aldehyde (0.83 g, 6.37 mmol) dissolved in tetrahydrofuran (6 mL). Following this, the reaction mixture was warmed to room temperature for 30 minutes. Once the reaction was complete it was worked up with water and ethyl acetate and the organic layer was washed with brine, dried over magnesium sulfate and concentrated. The yellow liquid was collected in 95% yield. $R_f$ 0.63 (DCM) $^1$H NMR (500 MHz, $CDCl_3$, ppm) d 7.49 (d, 2H, J=7.6 Hz), 7.33 (Ar, m, 1H), 7.32 (d, 2H, J=7.6 Hz), 7.14 (t, 1H, J=7.6 Hz), 7.04 (d, 2H, J=7.3 Hz), 5.68 (d, 1H, J=7.0 Hz), 2.47 (s, 6H); $^{13}$C NMR (125 MHz, $CDCl_3$, ppm) d 140.7, 131.8, 128.7, 128.2, 128.2, 126.6, 122.0, 121.6, 94.9, 86.4, 84.3, 82.3, 53.3, 20.9; HR MS (EI) m/z calculated. 260.120115, found 260.120251.

1-(2,6-Dimethyphenyl)-5-phenyl-1,4-pentadiyn-3-al:

$C_{19}H_{14}O$, FW=258.31 g/mol. 1-(2,6-Dimethylphenyl)-5-phenyl-1,4-pentadiyn-3-ol (1.57 g, 6.03 mmol) and manganese dioxide (3.15 g, 36.2 mmol) were combined in dichloromethane (35 mL) and stirred at room temperature for 40 minutes. Following completion of the reaction, the reaction mixture is filtered through celite, concentrated and the orange liquid product is isolated in 93% yield. $R_f$ 0.90 (DCM) $^1$H NMR (500 MHz, $CDCl_3$, ppm) d 7.61 (d, 2H, J=7.3 Hz), 7.48 (t, 1H, J=7.6 Hz), 7.40 (Ar, m, 3H), 7.08 (d, 2H, J=7.6 Hz), 2.52 (s, 6H); 13C NMR (125 MHz, $CDCl_3$, ppm) d 160.7, 143.2, 133.3, 131.2, 131.0, 128.8, 127.2, 119.6, 119.3, 97.8, 91.5, 90.6, 89.6, 20.9; HR MS (EI) m/z calculated. 258.104465, found 258.104127.

2-(2,6-Dimethylphenyl)-6-phenyl-thiopyran-4-one:

$C_{19}H_{16}OS$, FW=292.40 g/mol. A solution of sublimed sulfur (0.22 g, 6.74 mmol) and sodium borohydride (0.34 g, 8.98 mmol) dissolved in a 0.25 M solution of sodium ethoxide in ethanol (56 mL) was heated to reflux until the color changed from green to white. At the same time, 1-(2,6-dimethylphenyl)-5-phenyl-1,4-pentadiyn-3-al (1.45 g, 5.60 mmol) was dissolved in a 0.25 M solution of sodium ethoxide in ethanol (56 mL). This solution was stirred at room temperature for 30 minutes and the reaction was monitored with thin layer chromatography to ensure that all of the 1-(2,6-dimethylylphenyl)-5-phenyl-1,4-pentadiyn-3-al had reacted with the ethoxide. Once this addition was complete the two solutions were combined and heated to reflux for an hour. The solution was filtered through celite, concentrate, and finally extracted with water and ethyl acetate. The organic extracts were combined, dried over magnesium sulfate, and concentrated. A 3:1 dichloromethane to ethyl acetate mixture was used to isolate the red liquid in 94% yield from a silica gel column. $R_f$ 0.82 (3:1 DCM:ethyl acetate) $^1$H NMR (300 MHz, CDCl$_3$, ppm) d 7.61 (d$_x$d$_y$, 2H, J=1.8 Hz, J=7.6 Hz), 7.48 (Ar, m, 3H), 7.25 (d, 1H, J=1.2 Hz), 7.12 (d, 2H, J=7.6 Hz), 6.84 (d, 1H, J=1.2 Hz), 2.88 (m, 6H); $^{13}$C NMR (125.5 MHz, CD$_3$CN, ppm) d 182.4, 154.7, 153.5, 136.0, 135.6, 134.4, 130.7, 129.6, 129.4, 129.2, 127.7, 126.6, 126.6, 126.3, 19.8.

2-(2,6-Dimethylphenyl)-6-phenyl-4-methylthiopyrylium Hexafluorophosphate:

$C_{20}H_{19}F_6PS$, FW=436.40 g/mol. 2-(2,6-Dimethylphenyl)-6-phenyl-thiopyran-4-one (1.54 g, 5.3 mmol) was dissolved in tetrahydrofuran (52 mL) and cooled to 0° C. A 1.4 M methylmagnesium bromide (0.63 g, 15.8 mmol) solution was added to this solution and the solution was stirred at room temperature for 20 minutes. Once the reaction was complete, the reaction mixture was poured into acetic acid and a 60% solution of hexafluorophosphoric acid was slowly added until the solution darkened. The reaction mixture was then poured into water and the green crystals were collected. These crystals were then recrystallized in acetonitrile and collected in 67% yield. $^1$H NMR (400 MHz, CD$_3$CN, ppm) d 8.85 (s, 1H), 8.36 (s, 1H), 8.01 (d, 2H, J=7.7 Hz), 7.79 (t, 1H, J=7.3 Hz), 7.71 (t, 2H, J=7.7 Hz), 7.44 (t, 1H, J=7.7 Hz), 7.30 (d, 2H, J=7.7 Hz), 2.95 (s, 3H), 2.15 (s, 6H); $^{13}$C NMR (125.5 MHz, CD$_3$CN, ppm) d 173.3, 169.7, 168.9, 138.6, 137.6, 135.3, 134.4, 133.3, 132.3, 131.1, 129.4, 129.2, 26.2, 20.5; UV(DCM): max 383 nm (log e 13,500±260 M$^{-1}$ cm$^{-1}$).; HR MS (EI) m/z calculated. 290.112923, found 290.112053.

4-[4-[2-(2,6-Dimethylphenyl)-6-phenyl]-4H-thiopyranylidene)methyl]-1,3-butadienyl-2-(2,6-dimethylphenyl)-6-phenyl-thiopyrylium Hexafluorophosphate:

$C_{43}H_{37}F_6PS_2$, FW=762.85 g/mol. Aniline (2.86 g, 30.0 mmol) and 1,1,3,3-tetramethoxypropane (1.99 g, 12.1) were dissolved in acetic acid (10 mL) and heated to 80° C. for 15 minutes. The solution was removed from the heat and a 60% solution of hexafluorophosphoric acid (2 mL) was slowly added. The reaction mixture was then poured into water (200 mL) and the anilinium hexafluorophosphate salt of 1,1,3,3-tetramethoxypropane, a yellow solid, was collected. Sodium acetate (0.041 g, 0.50 mmol), the anilinium salt (0.084 g, 0.23 mmol), and 2-(2,6 dimethylphenyl)-6-(phenyl)-4-methylthiopyrylium hexafluorophosphate (0.20 g, 0.46 mmol) are combine in a flask containing acetic anhydride (1.2 mL) and acetic acid (1.2 mL). The reaction is heated to 95° C. for 4 minutes. Once the reaction is complete, the reaction mixture is poured into water and the brown precipitate is filtered off. The precipitate is dissolved in acetonitrile and crystallized out with ether. The resulting copper crystals are collected in 42% yield. UV(DCM): max 867 nm V. t-butyl-phenyl dye has the following chemical reaction:

A description of that chemical reaction is set forth below to form 4-[4-[2-(1,1-Dimethylethyl)-6-phenyl]-4H-thiopyranylidene)methyl]-1,3-butadienyl-2-(1,1-dimethylethyl)-6-phenyl-thiopyrylium hexafluorophosphate. The description is as follows:

1-(1,1-Dimethylethyl)-5-phenyl-1,4-pentadiyn-3-ol $(C_{15}H_{16}O)$, FW=212.29 g/mol. In an argon atmosphere 3,3 dimethyl-1-butyne (2.33 g 28.4 mmol) was dissolved in anhydrous tetrahydrofuran (60 mL) and cooled to −78° C. To this, 1.6 M n-butyllithium (4.90 g, 28.4 mmol) in hexanes, was added dropwise. The reaction was warmed to 20° C. for twenty minutes, and cannulated into a solution of phenylpropargyl aldehyde (3.69 g, 28.4 mmol)

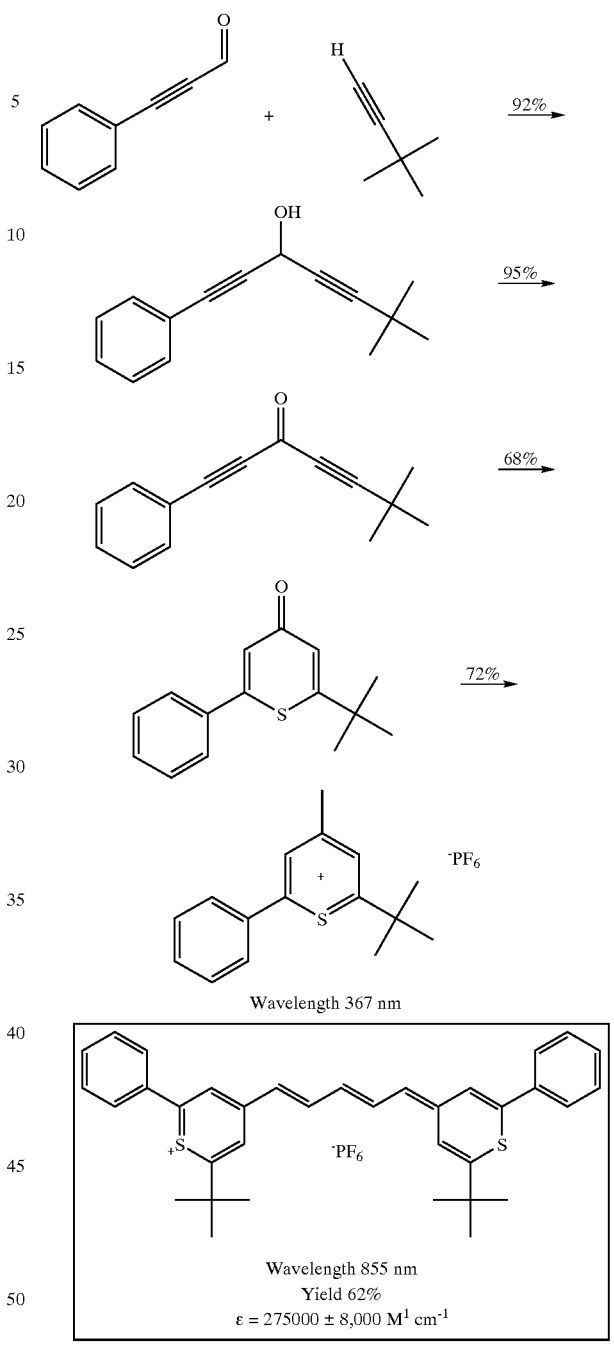

Wavelength 367 nm

Wavelength 855 nm
Yield 62%
$\varepsilon = 275000 \pm 8,000$ M$^{-1}$ cm$^{-1}$ dissolved in anhydrous tetrahydrofuran (30 mL) which was cooled to −78° C. The reaction was warmed to room temperature and stirred for an additional 20 minutes. The reaction was worked up with water and ethyl acetate and the organic layer was washed with brine, dried over magnesium sulfate and concentrated. The brown liquid was collected in 92% yield. $R_f$=0.52 (DCM) $^1$H NMR (500 MHz, CDCl$_3$, ppm): d 7.44 (Ar, m, 2H), 7.29 (Ar, m, 3H), 5.32 (d, 2H, J=7.2 Hz), 1.23 (s, 9H); $^{13}$C NMR (125 MHz, CDCl$_3$, ppm): d 131.8, 128.6, 128.2, 122.2, 93.4, 87.0, 83.6, 76.1, 52.7, 30.7, 27.3; HRMS(EI) m/z calculated 212.120115, found 212.120211.

1-(1 1-Dimethylethyl)-5-phenyl-1,4-pentadiyn-3-al:

$(C_{15}H_{14}O)$, FW=210.27 g/mol. 1-(1,1-dimethylethyl)-5-phenyl-1,4-pentadiyn-3-ol (5.46 g, 25.6 mmol) was dissolved in dichloromethane (134 mL). Manganese dioxide (13.42 g, 154 mmol) was added and the reaction was heated to reflux for 45 minutes. The reaction mixture was cooled and filtered through celite and concentrated. The orange liquid was obtained in 95% yield. $R_f$ 0.72 (DCM) $^1$H NMR (500 MHz, CDCl$_3$, ppm) d 7.59 (d, 2H, J=7.3 Hz), 7.46 (t, 1H, J=7.3 Hz), 7.38 (t, 2H, J=7.3 Hz) 1.32 (s, 9H); $^{13}$C NMR (75 MHz, CDCl$_3$, ppm) d 161.3, 133.2, 131.0, 128.6, 119.6, 102.6, 90.3, 89.4, 80.8, 29.8, 27.9; HRMS(EI) m/z calculated 210.104465, found 210.103678.

2-(1,1-Dimethyl)-6-phenyl-thiopyran-4-one:

(C$_{15}$H$_{16}$OS), FW=244.35 g/mol. A solution of sublimed sulfur (0.94 g, 29.3 mmol) and sodium borohydride (1.48 g, 39.0 mmol) in a 0.25 M solution of sodium ethoxide in ethanol (488 mL) was heated to reflux until the color changed from green to white. At the same time, 1-(1,1-dimethyl)-5-phenyl-1,4-pentadiyn-3-al (5.13 g, 24.4 mmol) was dissolved in a 0.25 M solution of sodium ethoxide in ethanol (488 mL). This solution was stirred at room temperature for 10 minutes and monitored with thin layer chromatography to ensure that the -(1,1-dimethyl)-5-phenyl-1,4-pentadiyn-3-al had been completely reacted with the ethoxide. Once this had happened, the two solutions were then combined and heated to reflux for an additional 10 minutes. Once the reaction was complete, the solution was first filtered through celite and then concentrated. After this, the reaction was extracted with water and ethyl acetate. The combined organic extracts were washed with brine, dried over magnesium sulfate and concentrated. Ethyl acetate was used to isolate the red liquid in 68% yield from a silica gel column. $R_f$=0.77 (EtOAc) $^1$H NMR (400 MHz, CDCl$_3$, ppm): d 7.57 (Ar, m, 2H), 7.45 (Ar, m, 2H), 7.10 (s, 1H), 7.00 (s, 1H), 1.40 (s, 9H); $^{13}$ C NMR (125 MHz CDCl$_3$, ppm): d 182.7, 165.9, 153.0, 136.3, 130.4, 129.1, 126.8, 126.2, 125.0, 38.3, 30.5; HRMS(EI) m/z calculated 244.093149, found 244.092187.

2-(1,1-Dimethylethyl)-6-phenyl-4-methylthiopyrylium Hexafluorophosphate:

(C$_{16}$H$_{19}$F$_6$PS), FW=388.35 g/mol. 2-(1,1-Dimethylethyl)-6-phenyl-thiopyran-4-one (4.05 g, 16.6 mmol) was dissolved in tetrahydrofuran (70 mL) and cooled to 0° C. A solution of 1.4 M methylmagnesium bromide (3.30 g, 82.8 mmol) was added and the reaction mixture was stirred at room temperature for 15 minutes. The solution was then poured into acetic acid and a 60% solution of hexafluorophosphoric acid was slowly added until the solution darkened. The reaction mixture was then poured into water and the green crystals were collected by filtration. The crystals were then recrystallized in acetonitrile and collected in 72% yield as a light green powder. Melting point 178° C.; $^1$H NMR (500 MHz, CD$_3$CN, ppm) d 8.64 (s, 1H), 8.56 (s, 1H), 7.95 (d, 2H, J=7.6 Hz), 7.76 (Ar, m, 1H), 7.70 (Ar, m, 7.70), 2.88 (s, 3H), 1.62 (s, 9H); $^{13}$C NMR (125.5 MHz, CD$_3$CN, ppm) d 186.1, 169.0, 167.4, 134.8, 134.7, 134.7, 134.4, 131.2, 129.3, 42.5, 30.9, 26.0; UV(DCM): $_{max}$ 367 nm (log e 41,400±800) M$^{-1}$ cm$^{-1}$; HR MS (EI) m/z calculated 242.112923, found 242.113032.

4-[4-[2-(1,1-Dimethylethyl)-6-phenyl]-4H-thiopyranylidene)methyl]-1,3-butadienyl-2-(1,1-dimethylethyl)-6-phenyl-thiopyrylium Hexafluorophosphate:

C$_{35}$H$_{37}$F$_6$PS$_2$, FW=666.76 g/mol. Aniline (2.86 g, 30.0 mmol) and 1,1,3,3-tetramethoxypropane (1.99 g, 12.1) were dissolved in acetic acid (10 mL) and heated to 80° C. for 15 minutes. The solution was removed from the heat and a 60% solution of hexafluorophosphoric acid (2 mL) was slowly added. The reaction mixture was then poured into water (200 mL) and the anilinium hexafluorophosphate salt of 1,1,3,3-tetramethoxypropane, a yellow solid, was collected. Sodium acetate (0.023 g, 0.28 mmol), the anilinium salt (0.051 g, 0.14 mmol), and 2-(phenyl)-6-(1,1-dimethylethyl)-4-methylthiopyrylium hexafluorophosphate (0.108 g, 0.28 mmol) are combined in a flask containing acetic anhydride (0.75 mL) and acetic acid (0.75 mL). The reaction is heated to 95° C. for 10 minutes. Once the reaction is complete, the reaction mixture is poured into water and the brown precipitate is filtered off. The precipitate is dissolved in acetonitrile and crystallized out with ether. The resulting copper crystals are collected in 62% yield. Melting point 206.5–207.5° C.; $^1$H NMR (500 MHz, CD$_3$CN, ppm) d 7.92 (t, 2H, J=13.7 Hz), 7.70 (d, 6H, J=7.6 Hz), 7.53 (Ar, m, 8H), 6.60 (t, 1H, J=12.5 Hz), 6.46 (d, 2H, J=13.4 Hz), 1.42 (s, 18H); $^{13}$C NMR (125.5 MHz, CD$_3$CN, ppm) d 167.1, 152.9, 151.7, 149.3, 136.8, 134.7, 132.2, 131.2, 130.5, 129.4, 127.8, 126.1, 40.1, 30.7; UV(DCM): $_{max}$ 855 nm (log e 275,000±8,000) M$^{-1}$ cm$^{-1}$.

VI. Para-isopropyl-phenyl dye and Ortho-isopropyl-phenyl dye: The preliminary steps to generate 4-[4-[2-(Isopropylphenyl)-6-phenyl]-4H-thiopyranylidene)methyl]-1,3-butadienyl-2-(isopropylphenyl)-6-phenyl-thiopyrylium hexafluorophosphate and for 4-[4-[2-(Isopropylphenyl)-6-phenyl]-4H-thiopyranylidene)methyl]-1,3-butadienyl-2-(isopropylphenyl)-6-phenyl-thiopyrylium hexafluorophosphate are as follows:

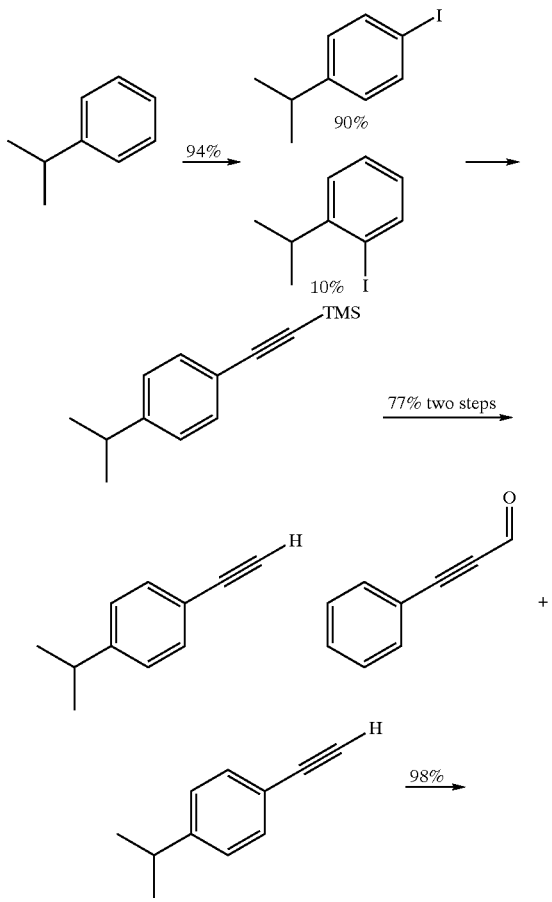

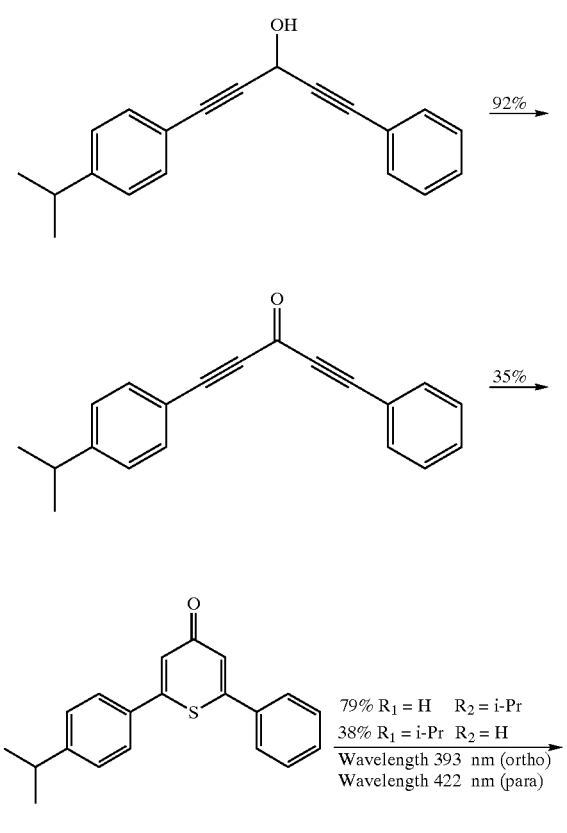

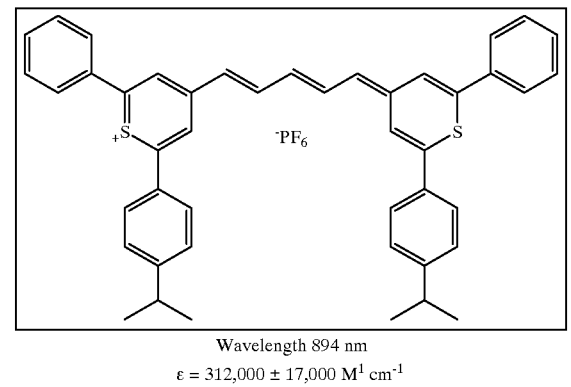

Wavelength 894 nm
$\varepsilon = 312{,}000 \pm 17{,}000\ M^{1}\ cm^{-1}$ and 4-[4-[2-(Isopropylphenyl)-6-phenyl]-4H-thiopyranylidene)methyl]-1,3-butadienyl-2-(isopropylphenyl)-6-phenyl-thiopyrylium hexafluorophosphate and for 4-[4-[2-(Isopropylphenyl)-6-phenyl]-4H-thiopyranylidene) methyl]-1,3-butadienyl-2-(isopropylphenyl)-6-phenyl-thiopyrylium hexafluorophosphate respectively are as follows:

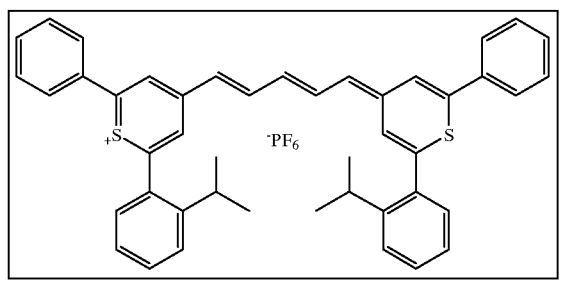

Wavelength 871 nm
$\varepsilon = 296{,}000 \pm 8{,}000\ M^{1}\ cm^{-1}$

The description of these reactions are set forth immediately below:

4-Isopropyl-iodobenzene:

($C_9H_{11}I$), FW=246.09 g/mol. Cumene (45.0 g, 377 mmol), iodine (38.25 g, 151 mmol) and iodic acid (15.38 g, 87.4 mmol) were dissolved in a solution of acetic acid (188 mL), water (30 mL), dichloromethane (19 mL), and sulfuric acid (7.5 mL). The solution was heated to 85° C. for three hours. Once the reaction was complete, the reaction was worked up with water and dichloromethane. The dichloromethane was washed with sodium hydrosulfite, dried over magnesium sulfate and concentrated, yielding a red liquid in 94% yield. $R_f$ 0.63 (hexanes) $^1$H NMR (300 MHz, CDCl$_3$, ppm) d 7.58 (d, 2H, J=8.3 Hz), 6.96 (s, 2H, J=8.3 Hz), 2.83 (septet, 1H, J=6.9 Hz), 1.20 (d, 6H, J=6.9 Hz); $^{13}$C NMR (75.5 MHz, CDCl$_3$, ppm) d 148.2, 137.2, 128.5, 90.7, 33.6, 23.8; LR MS (EI) m/z 246.

4-(Trimethylsilylethynyl)-isopropylphenyl:

($C_{14}H_{20}Si$), FW=216.39 g/mol. 4-Isopropyl-iodobenzene (5.00 g, 20.3 mmol), copper iodide (0.08 g, 0.40 mmol), triphenylphosphine (0.27 g, 1.0 mmol), and bis(triphenylphosphine)palladium(II) chloride (0.28 g, 0.40 mmol) were dissolved in piperidine (25 mL). (Trimethylsilyl)acetylene (2.59 g, 26.4 mmol) was added and the reaction mixture was stirred at room temperature for 2 hours. Once the reaction was complete, the reaction mixture was filtered through celite and extracted with water and hexanes. The hexanes were washed with brine, dried over magnesium sulfate and concentrated, yielding a yellow liquid which was taken on without purification. $R_f$ 0.5 (hexanes) $^1$H NMR (500 MHz, CDCl$_3$, ppm) d 7.37 (d, 2H, J=8.5 Hz), 7.13 (d, 2H, J=8.0 Hz), 2.86 (m, 1H, J=6.7 Hz), 1.22 (d, 6H, J=7.3 Hz), 0.03 (s, 9H); $^{13}$C NMR (75 MHz, CDCl$_3$, ppm) d 149.5, 131.9, 126.3, 120.4, 105.4, 34.0, 23.8, 0.00.

4-(Ethynyl)-isopropylphenyl:

($C_{11}H_{12}$), FW=144.22 g/mol. 4-(Trimethylsilylethynyl)-isopropylphenyl (4.39 g, 20.3 mmol) was dissolved in tetrahydrofuran (40 mL) and water (4 mL). This reaction mixture was cooled to 0 C and tetrabutylammonium fluoride (6.54 g, 25.0 mmol) was added dropwise. Following this addition, the reaction was stirred at room temperature for 8 hours. The reaction was then extracted with water and hexane. The hexane was dried over magnesium sulfate and concentrated yielding a yellow liquid in 77% yield. $R_f$ 0.45 (hexanes) $^1$H NMR (500 MHz, CDCl$_3$, ppm) d 7.45 (d, 2H, J=8.2 Hz), 7.20 (d, 2H, J=8.2 Hz), 3.04 (s, 1H), 2.91 (m, 1H, J=6.9 Hz), 1.26 (d, 6H, J=7.1 Hz); $^{13}$C NMR (75 MHz, CDCl$_3$, ppm) d 149.7, 132.1, 126.4, 119.4, 83.8, 76.4, 34.0, 23.7; HR MS (EI) m/z calculated 144.093900, found 144.093873.

1-(4-Isopropylphenyl)-5-phenyl-1,4-pentadiyn-3-ol:

$C_{20}H_{18}O$, FW=274.36 g/mol. 4-(Ethynyl)-isopropylphenyl (2.14 g, 20.9 mmol) is dissolved in tetrahydrofuran (40 mL) and cooled to −78° C. A 1.6 M nBuLi (3.61 g, 20.9 mmol) in hexanes was added dropwise and the reaction was warmed to room temperature for 20 minutes. This reaction mixture was then transferred to a solution of phenylpropargyl aldehyde (5.60 g, 20.9 mmol) dissolved in tetrahydrofuran (20 mL). Following this, the reaction mixture was warmed to room temperature for 30 minutes. Once the reaction was complete it was worked up with water and ethyl acetate and the organic layer was washed with brine, dried over magnesium sulfate and concentrated. The brown liquid was collected in 98% yield. $R_f$ 0.56 (DCM) $^1$H NMR (500 MHz, CDCl$_3$, ppm) d 7.48 (Ar, m, 2H), 7.40 (d, 2H, J=8.1 Hz), 7.32 (Ar, m, 3H), 7.17 (d, 2H, J=8.1 Hz), 5.55 (d, 1H, J=7.0 Hz) 2.88 (m, 1H), 1.22 (d, 6H, J=6.9 Hz).

1-(4-Isopropylphenyl)-5-phenyl-1,4-pentadiyn-3-al:

$C_{20}H_{16}O$, FW=272.34 g/mol. 1-(4-Isopropylphenyl)-5-phenyl-1,4-pentadiyn-3-ol (5.65 g, 20.6 mmol) and manganese dioxide (10.74 g, 124 mmol) were combined in dichloromethane (41 mL) and heated to reflux for 30 minutes. Following completion of the reaction, the reaction mixture is filtered through celite, concentrated and the orange liquid product is isolated in 92% yield. $R_f$ 0.87 (DCM) $^1$H NMR (500 MHz, CDCl$_3$, ppm) d 7.63 (d, 2H, J=7.0 Hz), 7.57 (d, 2H, J=8.4 Hz), 7.46 (d, 1H, J=7.3 Hz), 7.40 (d, 2H, J=7.7 Hz), 7.29 (Ar, m, 2H) 2.93 (m, 1H), 1.24 (d, 6H, J=7.0 Hz); HR MS (EI) m/z calculated 272.120115, found 272.119612.

2-(4-Isopropylphenyl)-6-phenyl-thiopyran-4-one:

$C_{20}H_{18}OS$, FW=306.43 g/mol. A solution of sublimed sulfur (0.73 g, 22.7 mmol) and sodium borohydride (1.15 g, 30.3 mmol) dissolved in a 0.25 M solution of sodium ethoxide in ethanol (378 mL) was heated to reflux until the color changed from green to white. At the same time, 1-(4-isopropylphenyl)-5-phenyl-1,4-pentadiyn-3-al (5.15 g, 18.9 mmol) was dissolved in a 0.25 M solution of sodium ethoxide in ethanol (378 mL). This solution was stirred at room temperature for 15 minutes and the reaction was monitored with thin layer chromatography to ensure that all of the 1-(4-Isopropylphenyl)-5-phenyl-1,4-pentadiyn-3-al had reacted with the ethoxide. Once this addition was complete the two solutions were combined and heated to reflux for an hour. The solution was filtered through celite, concentrate, and finally extracted with water and ethyl acetate. The organic extracts were combined, dried over magnesium sulfate, and concentrated. A 3:1 dichloromethane to ethyl acetate mixture was used to isolate the red liquid in 35% yield from a silica gel column. $R_f$ 0.57 (3:1 DCM:ethyl acetate) $^1$H NMR (300 MHz, CDCl$_3$, ppm) d 7.50 (Ar, m, 2H), 7.45 (d, 2H, J=8.2 Hz), 7.36 (Ar, m, 2H), 7.23 (d, 2H, J=8.0 Hz), 7.10 (Ar, m, 1H), 2.88 (m, 1H) 1.62 (d, 6H, J=6.9 Hz); $^{13}$C NMR (125.5 MHz, CD$_3$CN, ppm) d 182.0, 152.9, 152.7, 151.7, 135.7, 133.1, 130.4, 129.0, 127.1, 126.6, 126.4, 126.4, 126.1, 33.6, 23.4; UV(DCM): $_{max}$ 299 nm; HR MS (EI) m/z calculated 306.107837, found 306.107632.

2-(2-Isopropylphenyl)-6-phenyl-thiopyran-4-one:

$C_{20}H_{18}OS$, FW=306.43 g/mol. A solution of sublimed sulfur (0.73 g, 22.7 mmol) and sodium borohydride (1.15 g, 30.3 mmol) dissolved in a 0.25 M solution of sodium ethoxide in ethanol (378 mL) was heated to reflux until the color changed from green to white. At the same time, 1-(4-isopropylphenyl)-5-phenyl-1,4-pentadiyn-3-al (5.15 g, 18.9 mmol) was dissolved in a 0.25 M solution of sodium ethoxide in ethanol (378 mL). This solution was stirred at room temperature for 15 minutes and the reaction was monitored with thin layer chromatography to ensure that all of the 1-(4-Isopropylphenyl)-5-phenyl-1,4-pentadiyn-3-al had reacted with the ethoxide. Once this addition was complete the two solutions were combined and heated to reflux for an hour. The solution was filtered through celite, concentrate, and finally extracted with water and ethyl acetate. The organic extracts were combined, dried over magnesium sulfate, and concentrated. A 3:1 dichloromethane to ethyl acetate mixture was used to isolate the red liquid in 35% yield from a silica gel column. $R_f$ 0.71 (3:1 DCM:ethyl acetate) $^1$H NMR (300 MHz, CDCl$_3$, ppm) d 7.59 (Ar, m, 1H), 7.46 (Ar, m, 3H), 7.44 (Ar, m, 1H), 7.24 (Ar, m, 3H), 6.91 (Ar, m, 1H), 3.14 (m, 1H) 1.21 (d, 6H, J=6.9 Hz); $^{13}$C NMR (125.5 MHz, CD$_3$CN, ppm) d 181.8, 153.8, 153.6, 146.8, 135.7, 134.1, 130.6, 130.2, 129.7, 129.2, 129.1, 126.9, 126.7, 126.2, 125.7, 29.7, 24.3; UV(DCM): $_{max}$ 294 nm; HR MS (EI) m/z calculated 306.107837, found 306.107632.

2-(4-Isoprovylphenyl)-6-phenyl-4-methylthiopyrylium Hexafluorophosphate:

$C_{21}H_{21}F_6PS_2$, FW=450.42 g/mol. 2-(4-Isopropylphenyl)-6-phenyl-thiopyran-4-one (1.20 g, 3.9 mmol) was dissolved in tetrahydrofuran (50 mL) and cooled to 0° C. A 1.4 M methylmagnesium bromide (0.47 g, 11.7 mmol) solution was added to this solution and the solution was stirred at room temperature for 15 minutes. Once the reaction was complete, the reaction mixture was poured into acetic acid and a 60% solution of hexafluorophosphoric acid was slowly added until the solution darkened. The reaction mixture was then poured into water and the green crystals were collected. These crystals were then recrystallized in acetonitrile and collected in 79% yield. Melting point 165° C.; $^1$H NMR (500 MHz, CD$_3$CN, ppm) d 8.6 8 (d, 2H, J=15.9 Hz), 8.00 (Ar, m, 4H), 7.73 (Ar, m, 3H), 7.60 (d, 2H, J=8.2 Hz), 3.07 (m, 1H), 2.92 (s, 3H) 1.30 (d, 6H, J=6.7 Hz); $^{13}$C NMR (125.5 MHz, CD$_3$CN, ppm) d 169.1, 167.7, 157.0, 134.6, 134.6, 134.6, 134.3, 132.2, 131.3, 131.3, 129.5, 129.5, 129.4, 129.3, 34.9, 26.2, 23.6; UV(DCM): $_{max}$ 422 nm (log e 41,000±1600 M$^{-1}$ cm$^{-1}$); HR MS (EI) m/z calculated. 304.128573, found 304.128143.

2-(2-Isopropylphenyl)-6-phenyl-4-methylthiopyrylium Hexafluorophosphate:

$C_{21}H_{21}F_6PS_2$, FW=450.42 g/mol. 2-(2-Isopropylphenyl)-6-phenyl-thiopyran-4-one (0.29 g, 0.9 mmol) was dissolved in tetrahydrofuran (7 mL) and cooled to 0° C. A 1.4 M methylmagnesium bromide (0.33 g, 2.8 mmol) solution was added to this solution and the reaction was stirred at room temperature for 15 minutes. Once the reaction was complete, the reaction mixture was poured into acetic acid and a 60% solution of hexafluorophosphoric acid was added until the solution darkened. The reaction mixture was then poured into water and the green crystals were collected. These crystals were then recrystallized in acetonitrile and collected in 38% yield. Melting point 164° C., $^1$H NMR (500 MHz, CD$_3$CN, ppm) d 8.80 (s, 1H), 8.43 (s, 1H), 7.99 (d, 2H, J=7.0 Hz), 7.79 (d, 1H, J=7.3 Hz), 7.70 (Ar, m, 4H), 7.42 (Ar, m, 2H), 3.04 (m, 1H), 2.95 (s, 3H), 1.25 (d, 6H, J=6.7 Hz); $^{13}$C NMR (125.5 MHz, CD$_3$CN, ppm) d 171.6, 170.4, 167.7, 148.5, 138.1, 135.1, 134.8, 134.4, 133.4, 133.1, 131.6, 131.3, 129.4, 127.5, 30.7, 26.3, 24.3; UV(DCM): $_{max}$ 393 nm (log e 18,000±100 M$^{-1}$ cm$^{-1}$); HR MS (EI) m/z calculated. 304.128573, found 304.128143.

4-[4-[2-(2-Isopropylphenyl)-6-phenyl]-4H-thiopyranylidene)methyl]-1,3-butadienyl-2-(2-isopropylphenyl)-6-phenyl-thiopyrylium Hexafluorophosphate:

$C_{45}H_{41}F_6PS_2$, FW=790.90 g/mol. Aniline (2.86 g, 30.0 mmol) and 1,1,3,3-tetramethoxypropane (1.99 g, 12.1) were dissolved in acetic acid (10 mL) and heated to 80° C. for 15 minutes. The solution was removed from the heat and a 60% solution of hexafluorophosphoric acid (2 mL) was slowly added. The reaction mixture was then poured into water (200 mL) and the anilinium hexafluorophosphate salt of 1,1,3,3-tetramethoxypropane, a yellow solid, was collected. Sodium acetate (0.023 g, 0.24 mmol), anilinium salt (0.044 g, 0.12 mmol), and 2-(2-Isopropylphenyl)-6-(phenyl)-4-methylthiopyrylium hexafluorophosphate (0.108 g, 0.24 mmol) are combine in a flask containing acetic anhydride (0.6 mL) and acetic acid (0.6 mL). The reaction is heated to 95° C. for 7 minutes. Once the reaction is complete, the reaction mixture is poured into water and the brown precipitate is filtered off. The precipitate is dissolved in acetonitrile and crystallized out with ether. The resulting copper crystals are collected in 47% yield. Melting point 206–207° C., $^1$H NMR (500 MHz, CD$_3$CN, ppm) d 7.97 (t, 2H, J=13.7 Hz) 7.87 (s, 3H), 7.77 (d, 4H, J=6.7 Hz), 7.56 (Ar, M, 9H), 7.34 (d, 4H, J=3.1 Hz), 6.74 (t, 1H, J=12.5 Hz), 6.60 (d, 2H, J=13.7 Hz), 3.16 (m, 1H), 1.24 (d, 12H, J=6.7 Hz); $^{13}$C NMR (125.5 MHz, CD$_3$CN, ppm) d 153.9, 153.6, 151.5, 150.0, 148.4, 136.4, 135.1, 132.5, 131.9, 131.5, 131.3, 130.6, 130.6, 129.5, 127.8, 127.5, 127.2, 126.9, 30.7, 24.4; UV(DCM): $_{max}$ 871 nm (log e 296,000±8,000 M$^{-1}$ cm$^{-1}$).

4-[4-[2-(4-Isopropylphenyl)-6-phenyl]-4H-thiopyranylidene)methyl]-1,3-butadienyl-2-(4-isopropylphenyl)-6-phenyl-thiopyrylium Hexafluorophosphate:

$C_{45}H_{41}F_6$ PS2, FW=790.90 g/mol. Aniline (2.86 g, 30.0 mmol) and 1,1,3,3-tetramethoxypropane (1.99 g, 12.1) were dissolved in acetic acid (10 mL) and heated to 80 C for 15 minutes. The solution was removed from the heat and a 60% solution of hexafluorophosphoric acid (2 mL) was slowly added. The reaction mixture was then poured into water (200 mL) and the anilinium hexafluorophosphate salt of 1,1,3,3-tetramethoxypropane, a yellow solid, was collected. Sodium acetate (0.023 g, 0.24 mmol), anilinium salt (0.044 g, 0.12 mmol), and 2-(4-Isopropylphenyl)-6-(phenyl)-4-methylthiopyrylium hexafluorophosphate (0.108 g, 0.24 mmol) are combined in a flask containing acetic anhydride (0.6 mL) and acetic acid (0.6 mL). The reaction is heated to 95 C for 8 minutes. Once the reaction is complete, the reaction mixture is poured into water and the brown precipitate is filtered off. The precipitate is dissolved in acetonitrile and crystallized out with ether. The resulting red crystals are collected in 63% yield. Melting point 165–167° C.; $^1$H NMR (500 MHz, CD$_3$CN, ppm) d 7.65 (t, 2H, J=19.4 Hz), 7.34 (d, 4H, J=7.33 Hz), 7.25 (s, 10H), 7.22 (d, 4H, J=6.6 Hz), 7.09 (d, 2H, J=7.7 Hz), 6.42 (t, 1H, J=12.1 Hz), 6.23 (d, 2H, J=13.6 Hz), 2.82 (m, 2H), 1.16 (d, 12H, 7.0 Hz); UV(DCM): $_{max}$ 893 nm (log e 312,000±17,000 M$^{-1}$ cm$^{-1}$).

Although variations in the embodiment of the present invention may not each realize all the advantages of the invention, certain features may become more important than others in various applications of the device. The invention, accordingly, should be understood to be limited only by the scope of the appended claims.

We claim:

1. A method for the synthesis of an intermediate dye product of having the following formula:

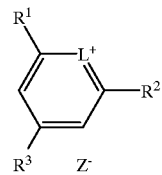

wherein

L is S, Te, or Se;

$R^1$ and $R^2$ are either the same or different aryl or alkyl compounds;

$R^3$ is hydrogen or a short chain alkyl group; and

Z is an anion, comprising the steps of:

reacting a $R^1$ acetylene compound with a $R^2$-acetylene compound to form an enol ether compound with the $R^1$ and $R^2$ constituents attached thereto; and reacting an L-based compound with the enol ether compound to obtain the intermediate dye product.

2. The method of claim 1 wherein the intermediate dye product is obtained at an overall yield of over 50%.

3. The method of claim 1 further comprising the step of reacting the intermediate dye product in a basic solution containing triethylamine to form a dye product having the following structure:

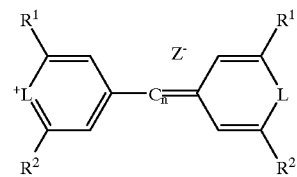

wherein Cn is a chain of linear or substituted alkenes having a length of from 1 to 5 carbons.

4. The method of claim 3 wherein the basic solution comprises sodium acetate, acetic acid, or acetic anhydride.

5. The method of claim 1 wherein $R^1$ and $R^2$ are aryl groups having 3 to 15 carbon atoms, linear alkyl groups having 1 to 15 carbon atoms, and branched alkyl groups having 1 to 15 carbon atoms.

6. The method of claim 5 wherein $R^1$ and $R^2$ groups are selected from the group consisting of methyl, ethyl, isopropyl, t-butyl, pentyl groups, phenyl, tolyl, ethylphenyl, naphthyl, and the following structures:

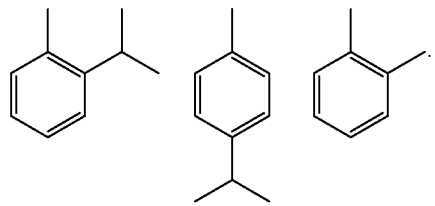

7. The method of claim 5 wherein the aryl group, the linear alkyl group, and branched alkyl group have at least one substituent thereon.

8. The method of claim 7 wherein the substituent is selected from the group consisting of aryl groups having 6 to 15 carbon atoms, halogen atoms and alkoxy groups having 1 to 5 carbon atoms.

9. The method of claim 1 wherein Z is an anion selected from the group consisting of halogen, trifluoroacetate, trichloroacetate, p-toluenesulfonate, perchlorate, periodate, tetrachloroaluminate, trichloroferrate (II), tetrafluoroborate, hexafluorophosphate, sulfate, hydrogensulfate and nitrate.

10. The method of claim 1 wherein n of Cn is 1–5.

11. The method of claim 3 wherein the dye product absorbs between 800 and 900 nm.

12. The method of claim 3 wherein claimed process makes the dye product at an overall yield of over 50%.

13. The method of claim 12 wherein the overall yield of the dye product is greater than 60%.

14. The method of claim 2 wherein the overall yield of the intermediate dye product is greater than 65%.

15. The method of claim 1 further comprising the step of adding a palladium catalyst when reacting the $R^1$ acetylene compound with the $R^2$-acetylene compound to form the enol ether compound.

* * * * *